(12) United States Patent
Zhu et al.

(10) Patent No.: US 9,988,614 B1
(45) Date of Patent: Jun. 5, 2018

(54) HIGH FIDELITY BBSI

(71) Applicant: New England Biolabs, Inc., Ipswich, MA (US)

(72) Inventors: Zhenyu Zhu, Beverly, MA (US); Aine Quimby, Newton, NH (US)

(73) Assignee: New England Biolabs, Inc., Ipswich, MA (US)

( * ) Notice: Subject to any disclaimer, the term of this patent is extended or adjusted under 35 U.S.C. 154(b) by 0 days. days.

(21) Appl. No.: 15/337,597

(22) Filed: Oct. 28, 2016

(51) Int. Cl.
*C12N 9/22* (2006.01)
*C12N 9/00* (2006.01)
*C12P 19/34* (2006.01)

(52) U.S. Cl.
CPC ............... *C12N 9/22* (2013.01); *C12N 9/93* (2013.01); *C12P 19/34* (2013.01); *C12Y 605/01001* (2013.01)

(58) Field of Classification Search
None
See application file for complete search history.

(56) References Cited

PUBLICATIONS

Ngo et al., in The Protein Folding Problem and Tertiary Structure Prediction, 1994, Merz et al. (ed.), Birkhauser, Boston, MA, pp. 433 and 492-495.*
Nasri, et al Nucleic Acids Res. 1986 14, 811.
Engler, et al PLoS One, 2008, 3: e3647.
Engler, et al PLoS One, 2009, 4: e5553.
Engler, Methods Mol. Biol. 2011 729:167-81.
Wei,et al, Nucl. Acids Res. 2008 36: e50.
Nelson, et al., Lehninger Principles of Biochemistry, Third Edition, 2000, Excerpts.

* cited by examiner

*Primary Examiner* — Richard G Hutson
(74) *Attorney, Agent, or Firm* — New England Biolabs, Inc; Harriet M. Strimpel

(57) ABSTRACT

A composition comprising a variant BbsI restriction endonuclease having reduced star activity is provided, as well as kits and methods employing the same.

19 Claims, 1 Drawing Sheet

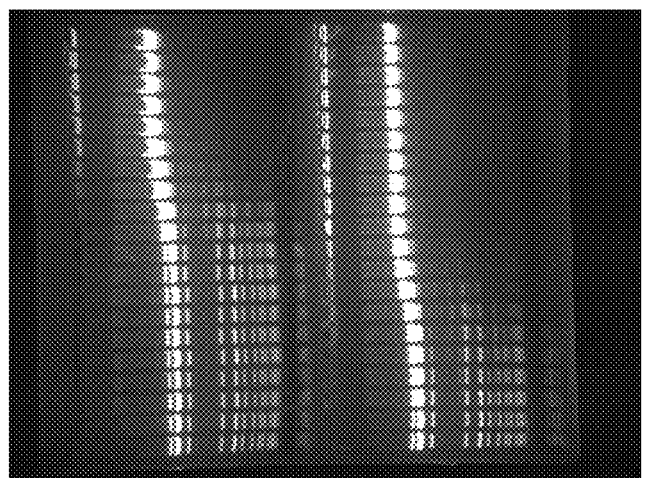
NEB4: FI ≥500 (1)
NEB3: FI ≥2 (1/256)
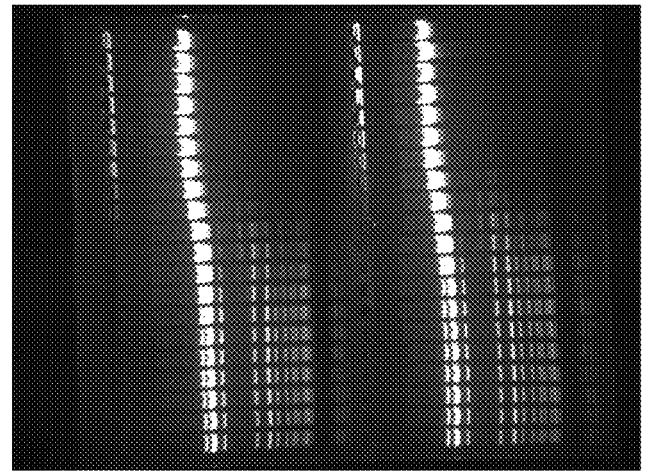
NEB2: FI ≥32 (1/16)
NEB1: FI ≥120 (1/4)

US 9,988,614 B1

HIGH FIDELITY BBSI

BACKGROUND

Under non-standard reaction conditions, some restriction endonucleases are capable of cleaving sequences which are similar, but not identical, to their defined recognition sequence. This altered specificity has been termed "star activity". It has been suggested that star activity is a general property of restriction endonucleases (Nasri, et al *Nucleic Acids Res.* 1986 14, 811). Consistent with this suggestion, many restriction endonucleases will cleave noncanonical sites under certain extreme conditions (e.g., high glycerol, high enzyme concentration, non-optimal buffer, prolonged reaction time and the presence of organic solvents or the presence of divalent cations that are not $Mg^{2+}$).

Star activity can be problematic for cloning, in some amplification reactions, in gene expression assays (e.g., SAGE) and for gene assembly.

There is a constant need for restriction endonucleases that have reduced star activity.

SUMMARY

Provided herein, among other things, is a composition comprising a variant BbsI restriction endonuclease having reduced star activity, wherein the variant BbsI restriction endonuclease comprises an amino acid sequence that differs from the amino acid sequence of the parent BbsI restriction endonuclease by a substitution at a position corresponding to position 442 of SEQ ID NO:2. Kits and methods that employ the variant BbsI restriction endonuclease are also provided.

In general, a composition is provided that includes a variant BbsI restriction endonuclease having reduced star activity, wherein the variant BbsI restriction endonuclease comprises a subunit A and a subunit B, where the subunit B of the variant BbsI restriction endonuclease comprises an amino acid sequence that differs from the amino acid sequence of the subunit B of the parent BbsI restriction endonuclease by a substitution at a position corresponding to position 442 of SEQ ID NO:2. For example, the variant BbsI restriction endonuclease may include an Alanine (Ala) at a position corresponding to position 442 of SEQ ID NO:2 which is a Proline (Pro).

In one aspect, the composition may include a non-naturally occurring buffering agent. In another aspect, the composition may include glycerol. In one aspect, the composition comprises a fragment of DNA comprising one or more recognition sequences for the variant BbsI restriction endonuclease. For example, the composition may include multiple fragments of DNA that each comprises at least one recognition sequence for the variant BbsI restriction endonuclease. In another aspect, the multiple fragments have compatible overhangs after cleavage by the BbsI variant. In another aspect, the composition may further comprises a ligase.

In general in one aspect, a kit is provided that includes (a) a variant BbsI restriction endonuclease of any prior embodiment; and (b) a concentrated buffer comprising a non-naturally occurring buffering agent. In one aspect, the variant BbsI restriction endonuclease comprises an Ala at a position corresponding to position 442 of SEQ ID NO:2. The kit may also include a ligase for example, T4 DNA ligase.

In general in one aspect, a method is provided for combining the variant BbsI restriction endonuclease described above with a fragment of DNA comprising a recognition sequence for the variant BbsI restriction endonuclease to produce a reaction mix; and incubating the reaction mix to cleave the fragment. In one aspect, the variant BbsI restriction endonuclease includes an Ala at a position corresponding to position 442 of SEQ ID NO:2. In another aspect, the reaction mix comprises multiple fragments of DNA that each include at least one recognition site for the variant BbsI restriction endonuclease. In another aspect, at least two of the cleavage products have compatible overhangs. In another aspect, the reaction mix further comprises a ligase, wherein the ligase ligates the compatible overhangs together.

BRIEF DESCRIPTION OF THE FIGURES

The skilled artisan will understand that the drawings, described below, are for illustration purposes only. The drawings are not intended to limit the scope of the present teachings in any way.

FIG. 1 shows four gels used to determine the fidelity index of a BbsI P442A mutant.

DETAILED DESCRIPTION OF EMBODIMENTS

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxyl orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

A "mutant" or "variant" protein may have one or more amino acid substitutions, deletions (including truncations) or additions (including deletions) relative to a wild-type. A variant may have less than 100% sequence identity to the amino acid sequence of a naturally occurring protein but may have an amino acid sequence that is at least 80%, at least 85%, at least 90%, at least 95%, at least 97%, at least 98% or at least 99% identical to the amino acid sequence of the naturally occurring protein. A fusion protein is a type of protein composed of a plurality of polypeptide components that are unjoined in their naturally occurring state. Fusion proteins may be a combination of two, three or even four or more different proteins. The term polypeptide includes fusion proteins, including, but not limited to, a fusion of two or more heterologous amino acid sequences, a fusion of a polypeptide with: a heterologous targeting sequence, a linker, an epitope tag, a detectable fusion partner, such as a fluorescent protein, β-galactosidase, luciferase, etc., and the like. A fusion protein may have one or more heterologous domains added to the N-terminus, C-terminus, and or the middle portion of the protein. If two parts of a fusion protein are "heterologous", they are not part of the same protein in its natural state.

The term "non-naturally occurring" refers to a composition that does not exist in nature. Variant proteins are non-naturally occurring. In some embodiments, "non-naturally occurring" refers to a protein that has an amino acid sequence and/or a post-translational modification pattern that is different to the protein in its natural state. A non-naturally occurring protein may have one or more amino acid substitutions, deletions or insertions at the N-terminus, the C-terminus and/or between the N- and C-termini of the protein. A "non-naturally occurring" protein may have an amino acid sequence that is different from a naturally occurring amino acid sequence (i.e., having less than 100% sequence identity to the amino acid sequence of a naturally occurring protein) but that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell.

In the context of a nucleic acid, the term "non-naturally occurring" refers to a nucleic acid that contains: a) a sequence of nucleotides that is different from a nucleic acid in its natural state (i.e. having less than 100% sequence identity to a naturally occurring nucleic acid sequence), b) one or more non-naturally occurring nucleotide monomers (which may result in a non-natural backbone or sugar that is not G, A, T or C) and/or c) may contain one or more other modifications (e.g., an added label or other moiety) to the 5'-end, the 3' end, and/or between the 5'- and 3'-ends of the nucleic acid.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

The term "corresponding" in the context of "corresponding positions" is intended to refer to amino acid residues that are across from one another when the two sequences are aligned.

BbsI is a Type IIS restriction endonuclease encoded by the BbsI gene of *Brevibacillus laterosporus*. The enzyme is composed of two subunits, subunit A and subunit B. The amino acid sequences of subunit A and B of the wild type BbsI enzyme are shown below as SEQ ID NO:1 and 2 respectively.

```
(BbsI subunit A)
                                            SEQ ID NO: 1
MSKIFKQKNNYTQPKVFRDGCVPREIVYLPGNPAEIVLSTGERKIASCLH

CPDAPCLSFKDHELQNSAFPEFPQDQSAAVCATNAIAWDNENGIPVVDNN

RCISCGICVDRCPVGAIYMIEEGIEINNNHIGDYLINLDEDDGDPSKIFG

EKMYLLSEVKRSGKLKIETDEVITNIYNQLALIDLDAQFPNIFSRNLLMT

LGTTCSIRRRGDVNVRMDAVLGPPGTNYGVMEVEFDSNALLDSPRNILDD

LAVLSSRYGINYSDITPVIVSIAFPNTRSEYWRVINDINNVLQIKINSIT

IGALILLIWNLKKVNFNTDSFYADSECMEIRSSIANIIGDNPNISIGGIL

EVAK-
```

```
(BbsI subunit B)
                                               SEQ ID NO: 2
MQRFPNPGSDIPTFIRIFQILHSYLKNNGSFSLDDMSSTLTYTNLASSSGYMGEQALRLS    60

TRNDRSRDPLYNQSKMYAELYRILGWIQSTEEKTLEFSFTYLGEHMASAKSNPLPLFQES   120

LLGINYPNEVISVKSDNKIRPFATILRCMLDLDEILCRDEMIIGPLSLNDVDNNYRVMID   180

MIRKIRREKNNNKELADALNKLSESTKIKVNTLHNYTRFPLAALKYSGWVSSDKIKIYKG   240

RGTMLKLTDEGRKRAEWIKSSIDIGAEISEHESKEDLDKIIRISFFKMLERSYFDISSIR   300

EELASEFADIEEIYRNKDILLSPYQTFRREKLESALGKYYKSEKNMIDEQAKKLPSDHLP   360

SYEVEKQKVLKSTIVLKEIVSDKPKFSNGIALQIHEKKAVYGEDIDNIVEQLIKEYETAD   420

KTVFYPLVANLFQLLGFPCENPRHGINYQRWDAIIVDDQYCIPIEIKSPSEEEFISVKAI   480

RQALENKIVLLSRKVHPTNFESPSFVVGFNSPNERADVGRLISDIYDTFGIKIAVFDLRT   540

LLILVVQKVLRGKTITMEQLRMLGGIIDVQDI*                              572
```

An amino acid substitution at position 442 of subunit B of this enzyme decreases star activity. The cognate recognition sequence for this GAAGAC.

A composition comprising a variant BbsI restriction endonuclease having reduced star activity is provided. The variant BbsI restriction endonuclease should contain subunits A and B of the BbsI restriction endonuclease, and subunit B of the variant BbsI restriction endonuclease should comprise an amino acid sequence that differs from the amino acid sequence of subunit B of the parent BbsI restriction endonuclease by a substitution at a position corresponding to position 442 of SEQ ID NO:2. The variant BbsI restriction endonuclease may contain other amino acid substitutions.

In some embodiments, subunit A of the variant BbsI restriction endonuclease may comprise an amino acid sequence that is at least 95% identical to (e.g., at least 96%, at least 97%, at least 98% or at least 9% identical to) SEQ ID NO:1, and subunit B of the variant BbsI restriction endonuclease may comprise an amino acid sequence that is at least 95% identical to (e.g., at least 96%, at least 97%, at least 98% or at least 9% identical to) SEQ ID NO:2, wherein subunit B of the variant BbsI restriction endonuclease comprises an amino acid that is not a Pro at a position corresponding to position 442 of SEQ ID NO:2. For example, the variant BbsI restriction endonuclease may comprise an Ala at that position. In some embodiments, the composition may comprise a non-naturally occurring buffering agent, e.g., Tris and/or one or more additives such as glycerol.

In some embodiments, the composition may comprise a fragment of DNA (e.g., a PCR product) comprising one or more cognate recognition sequences for the variant BbsI restriction endonuclease. In these embodiments, both ends of the fragment may contain a cognate recognition sequence for the variant BbsI restriction endonuclease. In some embodiments, the composition may comprise multiple (e.g., 2, 3, 4, or 5 or more) fragments of DNA that each comprise at least one recognition sequence for the variant BbsI restriction endonuclease. In some embodiments, both ends of the fragments contain cognate recognition sequences for the variant BbsI restriction endonuclease. In these embodiments, the multiple fragments may have compatible overhangs after they are cleaved by the BbsI variant, thereby allowing them to be ligated together in an ordered, predetermined manner. In some embodiments, the composition may further comprise a ligase, e.g., T4 DNA ligase.

Also provided is a method. In some embodiments, this method may comprise combining the variant BbsI restriction endonuclease as described above with a fragment of DNA comprising one or more recognition sequences for the variant BbsI restriction endonuclease and a suitable buffer to produce a reaction mix and incubating the reaction mix to cleave the fragment. In some cases, both ends of the fragment may contain recognition sequences for the variant BbsI restriction endonuclease. In some embodiments, the reaction mix may comprise multiple fragments of DNA that each comprises at least one recognition sequence for the variant BbsI restriction endonuclease. Again, the recognition sequences may be at both ends of the fragments. In these embodiments, the variant BbsI restriction endonuclease may cleave the fragments to produce at least two cleavage products that have compatible overhangs. In some cases, the reaction mix may further comprise a ligase and the ligase ligates the compatible overhangs together. Such "one-pot" digest/ligation reactions are generally employed in so called "Golden Gate" assembly methods (see, e.g., Engler et al PLoS ONE 3: e3647; Engler et al PLoS ONE 4: e5553; and Engler Methods Mol. Biol. 2011 729:167-81). As such, the variant BbsI restriction endonuclease described herein may be used in such methods.

Also provided by this disclosure are kits for practicing the subject method, as described above. In certain embodiments, the kit may comprise: (a) the variant BbsI restriction endonuclease (b) a concentrated buffer (e.g., a 5× or 10× concentrate) comprising a non-naturally occurring buffering agent. In some embodiments, the kit may additionally contain any one or more of the components listed above, e.g., a ligase such as T4 DNA ligase. The various components of the kit may be present in separate containers or certain compatible components may be precombined into a single container, as desired. In addition to the probe, the kit may contain any of the additional components used in the method described above, e.g., a buffer, etc.

In addition to above-mentioned components, the subject kits may further include instructions for using the components of the kit to practice the subject methods, i.e., instructions for sample analysis.

All references cited herein are incorporated by reference.

EXAMPLES

Aspects of the present teachings can be further understood in light of the following examples, which should not be construed as limiting the scope of the present teachings in any way.

In order to identify a variant of BbsI that has reduced star activity, several variants of BbsI were made. The fidelity index (FI) for each variant and for wild type BbsI was determined using the method described in Wei et al (Nucl. Acids Res. 2008 36: e50). In this method, reactions containing the same amount of DNA and a serial dilution of each enzyme were performed using NEB buffers NEB1, NEB2, NEB3 and NEB4. The reaction products were run on a gel and quantified. In a typical gel, from left to right, each reaction contains the same amount of DNA that contains a recognition site for the enzyme, but the amount of enzyme is reduced as a 2-fold serial dilution across the gel. At the far right of the gel, there is very little enzyme, so little or no DNA is digested. As the amount increases toward the left, partially digested fragments start to appear, which eventually become fully digested when the amount of the enzyme reaches a critical point. This point corresponds to the lowest amount of enzyme needed for complete cleavage on cognate sites. At this point, all bands that can only be generated by this specific enzyme cleaving at its designated recognition sequence reach their highest intensities, and no other bands are present. This gives rise to the unique cleavage pattern that can be predicted based on the DNA sequence of the substrate and the recognition sequence of the enzyme. This pattern remains as the amount of the enzyme continues to increase until the star activity of the enzyme begins to appear. The amount of the restriction endonuclease for the lane that immediately precedes the initial star activity lane will be considered the highest amount showing no star activity. Once star activity appears, the normal cleavage band(s) is further cleaved into smaller fragments, visible as a weakening of the normal band(s) and the appearance of a new star activity band(s). The FI (fidelity index), which provides a measure of the amount of star activity for a restriction endonuclease, is defined as the ratio of the highest restriction endonuclease amount showing no star activity to the lowest restriction endonuclease amount needed for completed cleavage on cognate sites.

Exemplary results for a variant that comprises a P442A amino acid substitution are shown in FIG. 1.

The fidelity indices for the P442A variant are as follows (where the number in the brackets is the relative activity):
NEB1: FI≥120 (¼);
NEB2: FI≥32 (¹⁄₁₆);
NEB3: FI≥2 (¹⁄₂₅₆);
NEB4: FI≥500 (1), The fidelity indices for wild type BbsI are as follows (where the number in the brackets is the relative activity):
NEB1: FI=32 (½);
NEB2: FI=120 (1);
NEB3: FI=64 (¼);
NEB4: FI=64 (1).
The overall improvement factor for the variant is ≥4.

What is claimed is:

1. A composition comprising a variant BbsI restriction endonuclease comprising a subunit A and a subunit B, wherein:
   the subunit A comprises an amino acid sequence that is at least 95% identical to SEQ ID NO:1, and
   the subunit B comprises an amino acid sequence that is at least 95% identical to SEQ ID NO:2, and wherein the amino acid at the position corresponding to amino acid 442 of SEQ ID NO:2 in the variant BbsI restriction endonuclease is not a Pro.

2. The composition of claim 1, wherein the amino acid at the position corresponding to amino acid 442 of SEQ ID NO:2 in the variant BbsI restriction endonuclease is an Ala.

3. The composition of claim 1, wherein the composition comprises a non-naturally occurring buffering agent.

4. The composition of claim 1, wherein the composition comprises glycerol.

5. The composition of claim 1, wherein the composition comprises a fragment of DNA comprising one or more recognition sequences for the variant BbsI restriction endonuclease.

6. The composition of claim 1, wherein the composition comprises multiple fragments of DNA that each comprises at least one recognition sequence for the variant BbsI restriction endonuclease.

7. The composition of claim 6, wherein the multiple fragments have compatible overhangs after they are cleavage by the BbsI variant.

8. The composition of claim 1, wherein the composition further comprises a ligase.

9. A kit comprising:
   (a) the composition of claim 1; and
   (b) a concentrated buffer comprising a non-naturally occurring buffering agent.

10. The kit of claim 9, wherein the amino acid at the position corresponding to amino acid 442 of SEQ ID NO:2 in the variant BbsI restriction endonuclease is an Ala.

11. The kit of claim 9, further comprising:
    (c) a ligase.

12. The kit of claim 11, wherein the ligase is T4 DNA ligase.

13. A method comprising:
    combining the composition of claim 1 with a fragment of DNA comprising a recognition sequence for the variant BbsI restriction endonuclease and a buffer to produce a reaction mix; and
    incubating the reaction mix to cleave the fragment.

14. The method of claim 13, wherein the amino acid at the position corresponding to amino acid 442 of SEQ ID NO:2 in the variant BbsI restriction endonuclease is an Ala.

15. The method of claim 13, wherein the reaction mix comprises multiple fragments of DNA that each comprises at least one recognition sequence for the variant BbsI restriction endonuclease.

16. The method of claim 14, wherein at least two of the cleavage products have compatible overhangs.

17. The method of claim 15, wherein the reaction mix further comprises a ligase, wherein the ligase ligates the compatible overhangs together.

18. The composition of claim 1, wherein:
   subunit A of the variant BbsI restriction endonuclease comprises an amino acid sequence that is identical to SEQ ID NO:1, and
   subunit B of the variant BbsI restriction endonuclease comprises an amino acid sequence that is identical to SEQ ID NO:2 with the exception that the amino acid at the position corresponding to amino acid 442 of SEQ ID NO:2 is not a Pro.

19. The composition of claim 18, wherein the amino acid at the position corresponding to amino acid 442 of SEQ ID NO:2 in subunit B is an Ala.

\* \* \* \* \*

SEQUENCE LISTING

<160> NUMBER OF SEQ ID NOS: 2

<210> SEQ ID NO 1
<211> LENGTH: 354
<212> TYPE: PRT
<213> ORGANISM: Brevibacillus laterosporus

<400> SEQUENCE: 1

```
Met Ser Lys Ile Phe Lys Gln Lys Asn Asn Tyr Thr Gln Pro Lys Val
1               5                   10                  15

Phe Arg Asp Gly Cys Val Pro Arg Glu Ile Val Tyr Leu Pro Gly Asn
            20                  25                  30

Pro Ala Glu Ile Val Leu Ser Thr Gly Glu Arg Lys Ile Ala Ser Cys
        35                  40                  45

Leu His Cys Pro Asp Ala Pro Cys Leu Ser Phe Lys Asp His Glu Leu
    50                  55                  60

Gln Asn Ser Ala Phe Pro Glu Phe Pro Gln Asp Gln Ser Ala Ala Val
65                  70                  75                  80

Cys Ala Thr Asn Ala Ile Ala Trp Asp Asn Glu Asn Gly Ile Pro Val
                85                  90                  95

Val Asp Asn Asn Arg Cys Ile Ser Cys Gly Ile Cys Val Asp Arg Cys
            100                 105                 110

Pro Val Gly Ala Ile Tyr Met Ile Glu Glu Gly Ile Glu Ile Asn Asn
        115                 120                 125

Asn His Ile Gly Asp Tyr Leu Ile Asn Leu Asp Glu Asp Asp Gly Asp
    130                 135                 140

Pro Ser Lys Ile Phe Gly Glu Lys Met Tyr Leu Leu Ser Glu Val Lys
145                 150                 155                 160

Arg Ser Gly Lys Leu Lys Ile Glu Thr Asp Glu Val Ile Thr Asn Ile
                165                 170                 175

Tyr Asn Gln Leu Ala Leu Ile Asp Leu Asp Ala Gln Phe Pro Asn Ile
            180                 185                 190

Phe Ser Arg Asn Leu Leu Met Thr Leu Gly Thr Thr Cys Ser Ile Arg
        195                 200                 205

Arg Arg Gly Asp Val Asn Val Arg Met Asp Ala Val Leu Gly Pro Pro
    210                 215                 220

Gly Thr Asn Tyr Gly Val Met Glu Val Glu Phe Asp Ser Asn Ala Leu
225                 230                 235                 240

Leu Asp Ser Pro Arg Asn Ile Leu Asp Leu Ala Val Leu Ser Ser
                245                 250                 255

Arg Tyr Gly Ile Asn Tyr Ser Asp Ile Thr Pro Val Ile Val Ser Ile
            260                 265                 270

Ala Phe Pro Asn Thr Arg Ser Glu Tyr Trp Arg Val Ile Asn Asp Ile
        275                 280                 285

Asn Asn Val Leu Gln Ile Lys Ile Asn Ser Ile Thr Ile Gly Ala Leu
    290                 295                 300

Ile Leu Leu Ile Trp Asn Leu Lys Lys Val Asn Phe Asn Thr Asp Ser
305                 310                 315                 320
```

Phe Tyr Ala Asp Ser Glu Cys Met Glu Ile Arg Ser Ser Ile Ala Asn
                325                 330                 335

Ile Ile Gly Asp Asn Pro Asn Ile Ser Ile Gly Gly Ile Leu Glu Val
            340                 345                 350

Ala Lys

<210> SEQ ID NO 2
<211> LENGTH: 572
<212> TYPE: PRT
<213> ORGANISM: Brevibacillus laterosporus

<400> SEQUENCE: 2

Met Gln Arg Phe Pro Asn Pro Gly Ser Asp Ile Pro Thr Phe Ile Arg
1               5                   10                  15

Ile Phe Gln Ile Leu His Ser Tyr Leu Lys Asn Asn Gly Ser Phe Ser
            20                  25                  30

Leu Asp Asp Met Ser Ser Thr Leu Thr Tyr Thr Asn Leu Ala Ser Ser
        35                  40                  45

Ser Gly Tyr Met Gly Glu Gln Ala Leu Arg Leu Ser Thr Arg Asn Asp
    50                  55                  60

Arg Ser Arg Asp Pro Leu Tyr Asn Gln Ser Lys Met Tyr Ala Glu Leu
65                  70                  75                  80

Tyr Arg Ile Leu Gly Trp Ile Gln Ser Thr Glu Glu Lys Thr Leu Glu
                85                  90                  95

Phe Ser Phe Thr Tyr Leu Gly Glu His Met Ala Ser Ala Lys Ser Asn
            100                 105                 110

Pro Leu Pro Leu Phe Gln Glu Ser Leu Leu Gly Ile Asn Tyr Pro Asn
        115                 120                 125

Glu Val Ile Ser Val Lys Ser Asp Asn Lys Ile Arg Pro Phe Ala Thr
    130                 135                 140

Ile Leu Arg Cys Met Leu Asp Leu Asp Glu Ile Leu Cys Arg Asp Glu
145                 150                 155                 160

Met Ile Ile Gly Pro Leu Ser Leu Asn Asp Val Asp Asn Asn Tyr Arg
                165                 170                 175

Val Met Ile Asp Met Ile Arg Lys Ile Arg Arg Glu Lys Asn Asn Asn
            180                 185                 190

Lys Glu Leu Ala Asp Ala Leu Asn Lys Leu Ser Glu Ser Thr Lys Ile
        195                 200                 205

Lys Val Asn Thr Leu His Asn Tyr Thr Arg Phe Pro Leu Ala Ala Leu
    210                 215                 220

Lys Tyr Ser Gly Trp Val Ser Ser Asp Lys Ile Lys Ile Tyr Lys Gly
225                 230                 235                 240

Arg Gly Thr Met Leu Lys Leu Thr Asp Glu Gly Arg Lys Arg Ala Glu
                245                 250                 255

Trp Ile Lys Ser Ser Ile Asp Ile Gly Ala Glu Ile Ser Glu His Glu
            260                 265                 270

Ser Lys Glu Asp Leu Asp Lys Ile Ile Arg Ile Ser Phe Phe Lys Met
        275                 280                 285

Leu Glu Arg Ser Tyr Phe Asp Ile Ser Ser Ile Arg Glu Glu Leu Ala
    290                 295                 300

Ser Glu Phe Ala Asp Ile Glu Glu Ile Tyr Arg Asn Lys Asp Ile Leu
305                 310                 315                 320

Leu Ser Pro Tyr Gln Thr Phe Arg Arg Glu Lys Leu Glu Ser Ala Leu
                325                 330                 335

-continued

```
Gly Lys Tyr Tyr Lys Ser Glu Lys Asn Met Ile Asp Glu Gln Ala Lys
            340                 345                 350

Lys Leu Pro Ser Asp His Leu Pro Ser Tyr Glu Val Lys Gln Lys
        355                 360                 365

Val Leu Lys Ser Thr Ile Val Leu Lys Glu Ile Val Ser Asp Lys Pro
            370                 375                 380

Lys Phe Ser Asn Gly Ile Ala Leu Gln Ile His Glu Lys Lys Ala Val
385                 390                 395                 400

Tyr Gly Glu Asp Ile Asp Asn Ile Val Glu Gln Leu Ile Lys Glu Tyr
                405                 410                 415

Glu Thr Ala Asp Lys Thr Val Phe Tyr Pro Leu Val Ala Asn Leu Phe
                420                 425                 430

Gln Leu Leu Gly Phe Pro Cys Glu Asn Pro Arg His Gly Ile Asn Tyr
            435                 440                 445

Gln Arg Trp Asp Ala Ile Ile Val Asp Asp Gln Tyr Cys Ile Pro Ile
            450                 455                 460

Glu Ile Lys Ser Pro Ser Glu Glu Glu Phe Ile Ser Val Lys Ala Ile
465                 470                 475                 480

Arg Gln Ala Leu Glu Asn Lys Ile Val Leu Leu Ser Arg Lys Val His
                485                 490                 495

Pro Thr Asn Phe Glu Ser Pro Ser Phe Val Val Gly Phe Asn Ser Pro
            500                 505                 510

Asn Glu Arg Ala Asp Val Gly Arg Leu Ile Ser Asp Ile Tyr Asp Thr
            515                 520                 525

Phe Gly Ile Lys Ile Ala Val Phe Asp Leu Arg Thr Leu Leu Ile Leu
            530                 535                 540

Val Val Gln Lys Val Leu Arg Gly Lys Thr Ile Thr Met Glu Gln Leu
545                 550                 555                 560

Arg Met Leu Gly Gly Ile Ile Asp Val Gln Asp Ile
                565                 570
```